United States Patent [19]

Kronner

[11] 3,945,377

[45] Mar. 23, 1976

[54] HIP PINNING TOOL

[76] Inventor: Richard F. Kronner, Rte. 2, Box 583, Roseburg, Oreg. 97470

[22] Filed: Jan. 24, 1975

[21] Appl. No.: 543,803

[52] U.S. Cl. ............................................ 128/92 EB
[51] Int. Cl.² .......................................... A61F 5/04
[58] Field of Search ............ 128/92 EB, 83 R, 92 B, 128/92 BA, 92 BB, 92 E, 92 EA

[56] References Cited
FOREIGN PATENTS OR APPLICATIONS

| 869,842 | 1/1953 | Germany | 128/92 EB |
| 168,885 | 1/1951 | Austria | 128/92 EB |
| 227,453 | 6/1943 | Switzerland | 128/92 EB |
| 942,013 | 1/1949 | France | 128/92 EB |
| 910,078 | 5/1946 | France | 128/92 EB |
| 248,631 | 5/1947 | Switzerland | 128/92 EB |

*Primary Examiner*—John D. Yasko
*Attorney, Agent, or Firm*—James D. Givnan, Jr.

[57] ABSTRACT

A tool for assisting the surgeon in the setting of a surgical nail within the head and neck of a femur, the tool including a clamp structure temporarily affixed to the femoral shaft to support an adjustable arm in parallel, offset relationship to the femur. A guide assembly is positionable along said arm to locate first and second guide assembly members adjacent the femur end said members being pivotally mounted to enable their positioning and locking within multiple planes for proper guidance of a guide pin, drill and nail assembly. Interchangeable guide members provide precise, sequential guidance of the above bone penetrating instrumentalities. Calibrations on the tool enable calculated corrections to be set into the tool components and preclude the taking of X-rays simply for verifying the projected path of the guide pin.

6 Claims, 5 Drawing Figures

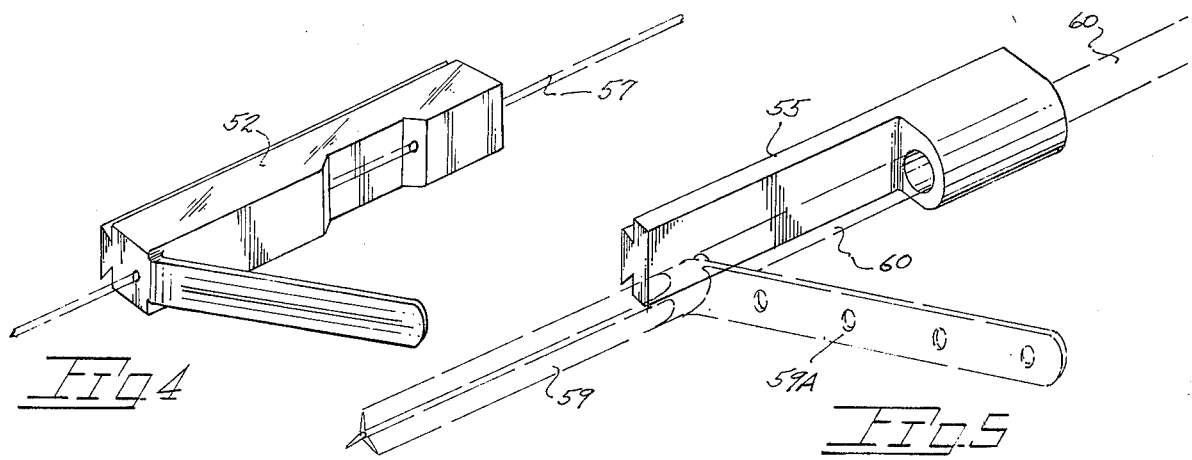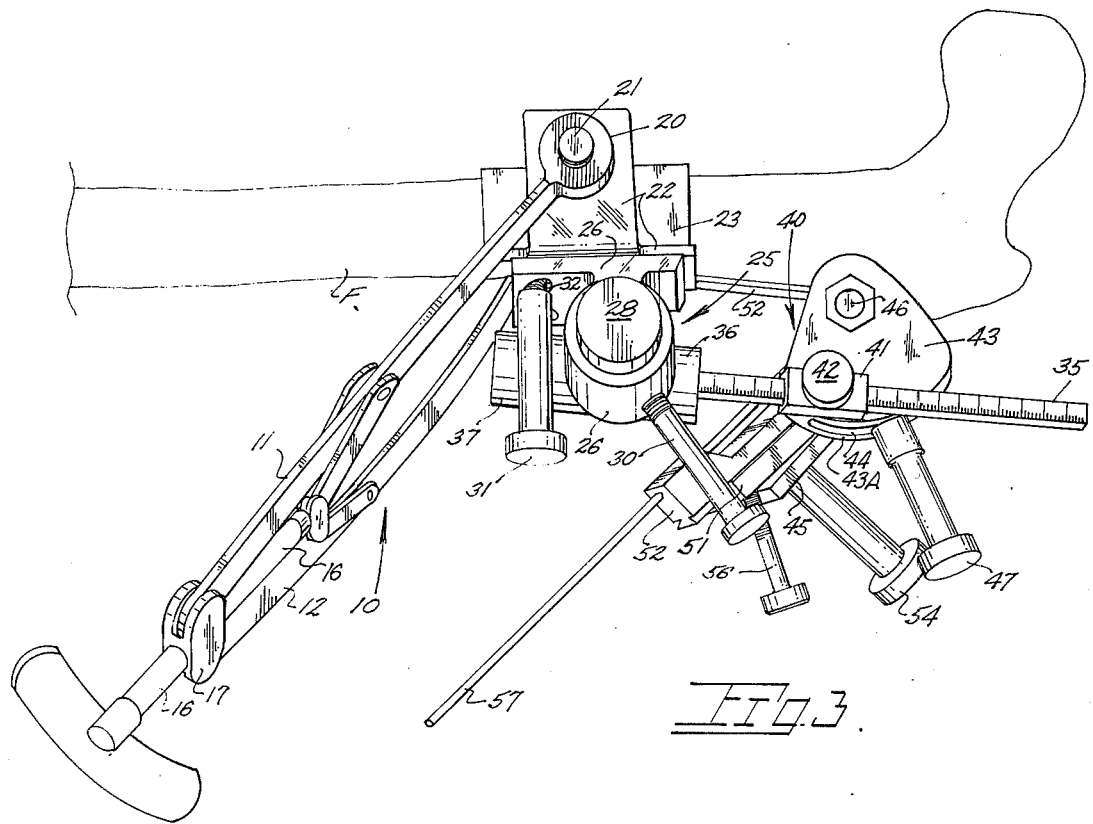

HIP PINNING TOOL

BACKGROUND OF THE INVENTION

The present invention is embodied within a tool for operating room use by a surgeon in hip pinning operations, the tool assuring proper guidance of the hip pin into place in an expeditious manner.

In repair of the head and neck portions of the femur, it is common practice to insert a metallic device, termed a nail, either of straight or angular configuration. The latter type of nail includes a side plate which is affixed to the femoral shaft by screws with the remaining angular portion extending through the femur neck. The nail so applied serves to reinforce the femur neck and immobilize same permitting knitting of the bone fragments. Such nails, with various modifications, have been in wide use for a considerable length of time and are well known in the medical field.

Proper placement of the nail entails the determination of the proper course for pin travel which determination is complicated by the angulated nature of the femur neck with respect to the surgically exposed upper end of the femoral shaft. The degree of angulation (in horizontal and vertical planes) may vary with each patient with the surgical problem further complicated by the absence of an immobile reference point. Accordingly, proper nail placement using present methods is dependent, to a large extent, on individual skill and judgment unaided by any surgical tool. Not unknown are instances of improperly placed pins necessitating a second setting of the pin.

At present, a rather complicated procedure is followed using multiple series of AP and lateral X-rays to disclose the position of an initially inserted guide pin resulting in a lengthy operation with any changes in guide pin location being plotted on the X-rays. Necessary calculations and changes in guide pin location can only be determined after the reading of each set of X-rays by the surgeon. Additionally, the patient is subjected to undesirable amounts of radiation. If correction of guide pin location is required, a second placement of the pin is accomplished along with a second series of AP and lateral X-rays for verification of pin location. Further, it is not uncommon to subject the patient to still another set of X-rays upon completion of a pinning operation to verify hip pin location.

SUMMARY OF THE INVENTION

The present tool is temporarily affixed to the femur to provide an immobile base on which a guide assembly is adjustably mounted to aid the surgeon in the calculation of a precise course for sequential entry of a guide pin, drill and hip pin.

The tool includes a clamp structure for attachment to the exposed upper femoral shaft, said clamp structure including a base supported in an immobile manner on the femur. Positionable relative to the clamp base is an arm assembly which is disposed generally along and offset from an upper segment of the femur. Means coupling the arm assembly to the fixed base permits full range adjustment of the arm to suit individual femur characteristics. Supported adjacent the distal end of the adjustable arm assembly is a pin and drill guide assembly offset from the upper end of the femoral shank. Pivoted first and second members of the guide assembly move about perpendicular axes to enable rotational positioning of the guide pin preparatory to the taking of AP and lateral X-rays. Further adjustment, if required upon reading of the X-rays, may be precisely made in degree and millimeter calibrations on the tool thereby dispensing with the need for additional preliminary X-rays.

Important objectives of the present invention include: the provision of a hip pinning tool for attachment in a fixed manner to the femur, said tool including multiple calibrated adjustments permitting precise setting of pin and drill components preparatory to bone entry; the provision of a hip pinning tool including guide means sequentially mounting the guide pin, drill and hip pin for travel along a known, projected course; the provision of a hip pinning tool greatly reducing the possibility of an inaccurately placed hip pin said tool having calibrated adjustments enabling the surgeon to set in both lineal and arcuate corrections prior to drilling the corrections being plotted from AP and lateral X-rays; the provision of a tool reducing the number of X-rays required in a hip pinning operation lessening radiation exposure of the patient and contributing significantly to curtailing operation duration.

BRIEF DESCRIPTION OF THE DRAWINGS

In the accompanying drawings:

FIG. 3 is a top plan view of FIG. 1, FIG. 4 is an upper perspective view of a pin guide removed from the guide holder, and FIG. 5 is an upper perspective view of the combination drill and hip nail guide removed from the guide holder.

DESCRIPTION OF THE PREFERRED EMBODIMENT

Figure 1:
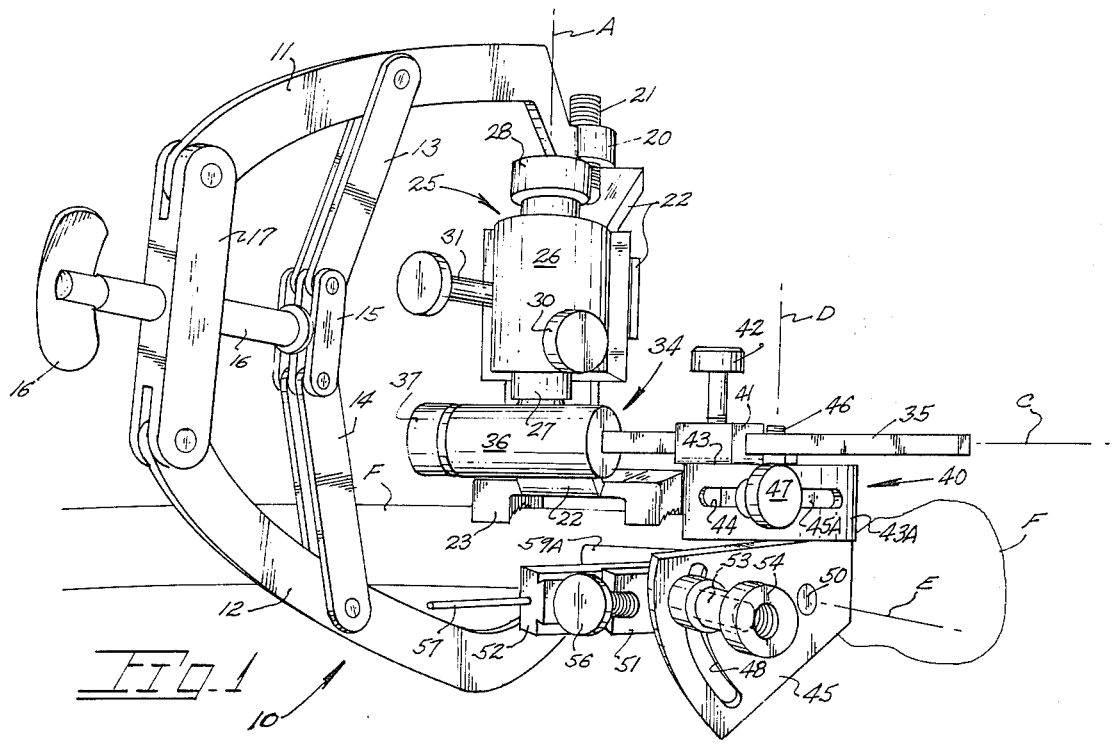
FIG. 1 is a front elevational view of the tool embodying the present invention operatively disposed adjacent the cephlad end of a femur.

With continuing reference to the accompanying drawings wherein applied reference numerals indicate parts similarly identified in the following specification, the reference numeral 10 indicates generally a clamp structure having upper and lower arms 11 and 12 with intermediate toggle linkage at 13 and 14 terminating inwardly in pivotal connection with a toggle control 15 actuated by a thumb screw 16 carried by a main body member 17 of the clamp with thumb screw rotation serving to open and close clamp arms 11 and 12 and associated clamp members at the distal ends of the arms into firm engagement with a femoral shaft of a femur indicated at F. Upper clamp arm 11 is fitted at its outer end with a threaded receptacle 20 within which is adjustably received a threaded stud 21 from which depends an angular base plate 22. The lower end of base plate 22 carries a femur engaging member 23 while oppositely a like member at 24 at the end of arm 12 firmly engages the femur. Base plate 22 constitutes a stationary base for the remaining tool structure and specifically a base for a boss 26 of spindle mounting means indicated generally at 25.

Mounting means 25 further includes a spindle 27 the upper portion of said spindle in threaded engagement with spindle knob 28 interiorly of boss 26. Control knob 28 and spindle 27 together provide a micrometer type adjustment for extension or retraction of spindle 27 along the spindle axis at A with a metric screw thread imparting travel with one rotation of the knob moving spindle 27 1 millimeter. Boss 26 is mounted for rotation about an axis at B by means of a horizontally disposed trunnion 29 extending in a pivoted manner through base plate 22. Accordingly, spindle 27 in addition to rectilinear adjustment along axis A may move about the horizontal axis at B of the trunnion as well during setting up of the tool. As spindle 27 is cylindrical, it of course, may also be rotated about axis A. A spindle locking screw at 30 extends through boss 26 and into abutment with spindle 27. A shouldered locking screw 31 extends through an arcuate slot 32 in a boss flange 26A and into base plate 22 to secure the boss in any adjusted relationship about axis B to the base plate 22.

Indicated generally at 34 is an arm assembly carried by spindle 27, the arm assembly including an arm 35 having incremental markings in relief and projecting in a horizontal manner outwardly from a holder 36 within which the inner or unseen end of the arm is slidably housed. An arm extension control at 37 is journalled within the opposite end of holder 36 in a captive manner by means of a snap ring or the like with a concealed portion of control 37 being in threaded engagement with a mating threaded extension at the inner end of arm 35. As in the above mentioned micrometer like adjustment for spindle 27, it is desirable that a metric screw thread be utilized for outward extension or retraction of said arm on a ratio of one turn to one millimeter of lineal arm movement to permit convenient repositioning of a later described guide assembly at 40. Provided along the upper surface of arm 35 are millimeter increments. In view of the immediately above described components, it will be understood that arm 35 is additionally extensible and retractable along an arm axis indicated at C.

Adjustably supported on arm 35 is a guide assembly indicated generally at 40 including an upper guide member 43 having a sleeve 41 thereon receiving said arm with a lock screw 42 abutting the arm. In the elevational view of FIG. 2, upper guide member 43 is of quadrant shape having a depending arcuate flange 43A slotted at 44. Disposed below upper guide member 43 is a lower guide member at 45 with pivot means at 46 interconnecting the members and permitting relative rotational movement therebetween about the vertical axis D of said pivot means. Lower guide member 45 includes a neck at 45A disposed inwardly of arcuate flange 43A which serves to receive a shouldered locking screw 47 which may be tightened into shoulder abutment with said flange to lock the lower guide member in place about axis D. As viewed in FIG. 1, lower guide member 45 is also of quadrant configuration with an arcuate slot 48 therein.

Swingably mounted at 50 to lower guide assembly member 45 is a guide holder 51 defining a lengthwise extending dovetail guideway within which various guides as at 52 may be temporarily mounted. Laterally projecting from holder 51 is a threaded stud 53 on which an internally threaded lock 54 is mounted, the latter engageable with the lower member 45 to lock holder 51 in place as adjusted about pivot 50. Holder 51 initially receives a guide at 52 which serves to mount a guide pin 57. A combination drill and hip nail guide 55 is later substituted for pin guide 52 with the latter guide 55 having a lengthwise extending bore corresponding to the drill diameter to guide the drill. Conventionally, the drill is additionally guided by the axially disposed guide pin. Pin guide 52 is removable from holder 51 and drill guide 55 substituted therefor during the course of a hip pinning operation. A set screw at 56 secures the interchangeable guides in place within holder 51.

In use, the clamp structure 10 is applied to the femoral shaft exposed by a standard length incision with major portions of clamp arms 11 and 12 remaining outside the anatomical areas of the lateral aspect of the leg and serving in the nature of retractors. With the clamp structure securely in place on the femur, arm 35 is positioned into parallel relationship with the femur whereupon guide assembly 40 is initially positioned along the arm to an approximate setting opposite that area of the lateral cortex through which an opening or window will be drilled. Standard AP and lateral X-rays are taken with the leading end of pin 57 positioned into place at the selected point of entry or window to be drilled in the lateral cortex. Projections of the pin path are drawn on the X-rays to indicate the course of the guide pin. Such projections enable the calculation by degrees and millimeters of any pin adjustment necessary within either the horizontal or vertical plane. Normally the guide pin will be initially set (about axis D) at 45 degrees included angle from the exposed femur cortex. Pin 57 will be approximately horizontal. The extension or retraction of arm 35 by control means 37 will enable a change to be made, if necessary, in the window location, the extent of such a change also being determined from the X-rays taken. Similarly, anterior to posterior course corrections for pin 57 may be readily determined from a comparison of the projected pin path to the desired pin path as scribed on a lateral X-ray. Any changes from the 45° included angle between the femur and the pin may be compensated for by movement of the lower guide member 45 about axis E of pivot 50. Normally, adjustment of components will be only about axes D and E and along axis C.

The surgeon will adjust the incrementally marked tool components for desired lineal and degree corrections with subsequent drilling of the window opening and passage of the guide pin 57 into the femur neck and head. Pin guide 52 is used initially to hold guide pin 57 during the taking of X-rays whereupon the guide pin is removed and a drill of like diameter substituted. Upon completion of drilling, guide pin 57 is re-installed and inserted into the drilled passageway seating forwardly within the femur head.

With guide pin 57 in position, pin guide 52 is removed from holder 51 and the combination drill and hip nail guide 55 substituted into place within holder 51. The combination drill and hip nail guide receives an open core drill bit, most commonly one-half inch in diameter, for a second drilling operation with the open core bit following guide pin 57 still in place within the femur neck and head. Upon completion of the half inch bore, the drill bit is removed with guide pin 57 being left in place for subsequent guidance of the hip nail. A hip nail 59, also having a central opening, is internally guided by the guide pin 57 and externally by a cylindrical rod 60 slidably disposed within combination drill and hip nail guide 55 and having its leading end in threaded engagement with a recess in the nail side plate 59A. Advancement of rod 60 seats the hip nail into place with the side plate of the nail coming to rest against the femoral shank whereat it is secured by screwing.

An alternate setting of the hip nail dispenses with the insertion of guide pin 57 into the femur neck and head.

In such instances the guide pin is used simply during the taking of AP and lateral X-rays. During reading of the X-rays projections of the guide pin are scribed to enable comparison of the projections with optimum nail placement. The guide pin is then removed along with its guide 52 and any corrective adjustments made of the tool components. As earlier noted the incremental markings on said components enable precise corrections, both lineal and arcuate, to be applied to reposition guide holder 51. Subsequently the combination drill and hip nail guide 55 is installed in holder 51 for drilling of the femur neck and head all without the previous installation of guide pin 57.

Figure 2:
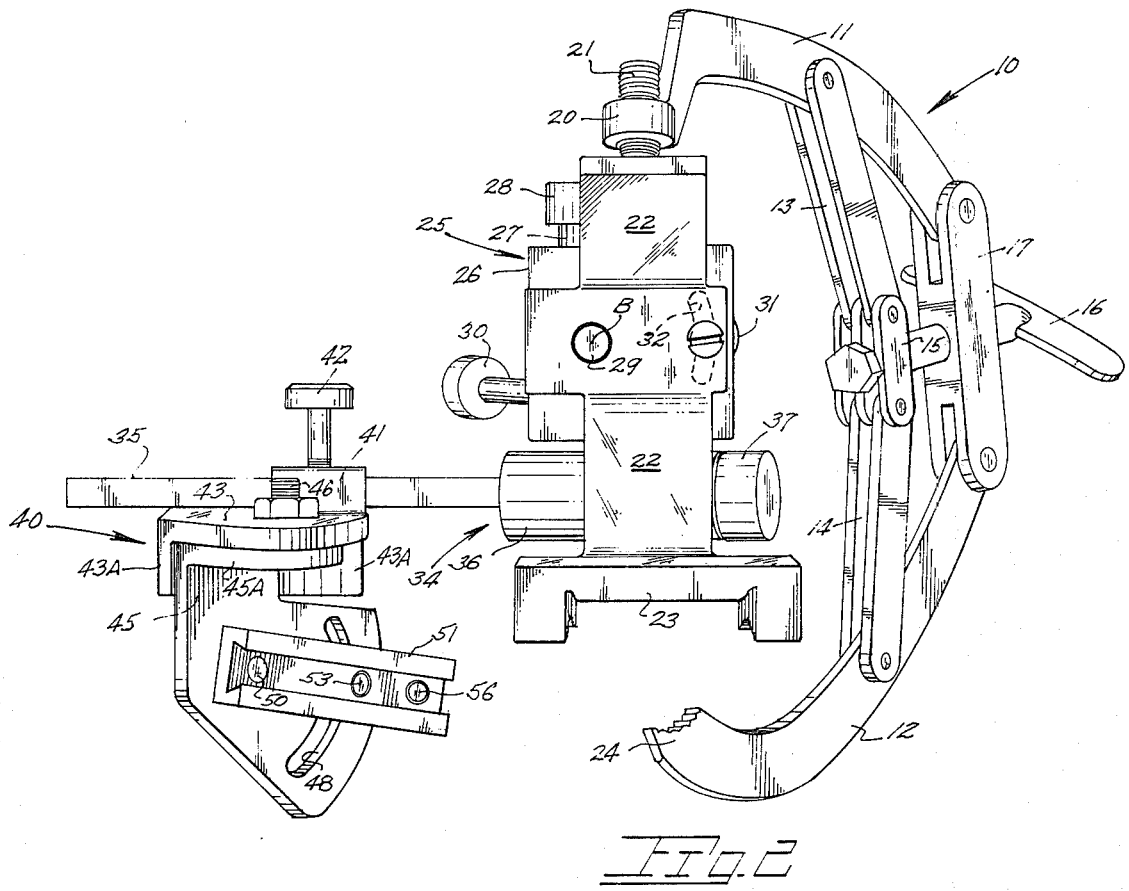
FIG. 2 is a rear elevational view of FIG. 1 with guide means removed from a guide holder.

While the drawings disclose a tool in use for installation of a hip nail in the left femur, the tool, of course, is equally adaptable for nail insertion into the right femur. Arm assembly 34 is positionable through 180° while clamp structure 10 is repositionable oppositely from the repositioned arm assembly. A second guide assembly, a mirror image of guide assembly 40 as shown in FIG. 1, is then applied to arm 35 with the remaining procedure as above described.

While I have shown but one embodiment of the invention it will be apparent to those skilled in the art that the invention may be embodied still otherwise without departing from the spirit and scope of the invention.

Having thus described the invention what is desired to be secured under a Letters Patent is:

1. A surgical tool adapted to be temporarily mounted to the femoral shaft for installation of a hip nail within the femoral neck and head in a precise manner, said tool comprising, a clamp structure including upper and lower pivoted clamping arms and a base supported in place by one of said clamping arms, said clamp structure adapted for clamped engagement with the femoral shaft, an arm assembly supported by said base including an arm positionable into offset relationship with the femoral shaft, mounting means adjustably mounting said arm assembly to said base of the clamp structure and permitting movement of said arm into said offset relationship, and a guide assembly adjustably supported by said arm and positionable opposite the cephlad end of the femur, said guide assembly including, upper and lower guide members adapted for movement relative to one another about an upright axis, means locking said upper and lower guide members in a desired relationship, a guide holder swingably mounted on the lower guide member for adjusted movement about a horizontal axis whereby said guide holder is positionable to compensate for antiversion or retroversion of the femur neck, means locking said guide holder to said lower member, said guide holder sequentially receiving a pin guide and drill guide, means interlocking the guide holder and said pin and drill guides.

2. The surgical tool claimed in claim 1 additionally including a combination drill guide and hip nail guide positionable within said guide holder during drilling and setting of the hip nail.

3. The surgical tool claimed in claim 1 wherein said mounting means additionally includes adjustment means for imparting vertical movement to said arm assembly.

4. The surgical tool claimed in claim 3 wherein said guide assembly additionally includes means in slidable engagement with said arm.

5. The surgical tool claimed in claim 4 wherein said mounting means is pivotally mounted on said base permitting adjusted movement of said mounting means and said arm assembly carried thereby about a horizontal axis.

6. The surgical tool claimed in claim 1 wherein said upper and lower pivoted clamping arms have medial segments engageable with anatomical areas which function in the nature of retractors.

* * * * *